United States Patent [19]

Crescentini et al.

[11] 4,311,642
[45] Jan. 19, 1982

[54] RECOVERY OF CAPROLACTAM FROM NYLON 6 OLIGOMERS

[75] Inventors: Lamberto Crescentini, Chester; Webb B. Blackman, Jr., Chesterfield; Joseph D. DeCaprio, Hopewell; William B. Fisher, Chester; Roy J. Lilley, Jr., Richmond; John W. Wagner, Petersburg, all of Va.

[73] Assignee: Allied Corporation, Morris Township, Morris County, N.J.

[21] Appl. No.: 187,864

[22] Filed: Sep. 17, 1980

[51] Int. Cl.$^3$ ............................................. C07D 201/12
[52] U.S. Cl. ............................................... 260/239.3 A
[58] Field of Search ................................. 260/239.3 A

[56] References Cited

U.S. PATENT DOCUMENTS

| | | | |
|---|---|---|---|
| 3,182,055 | 5/1965 | Bonfield et al. | 260/239.3 A |
| 3,245,964 | 4/1966 | Wiesner et al. | 260/239.3 A |
| 3,266,165 | 8/1966 | Apostle et al. | 260/239.3 A |
| 3,294,756 | 12/1966 | Russell et al. | 260/239.3 A |
| 3,373,145 | 3/1968 | Wagner | 260/239.3 A |
| 3,449,220 | 6/1969 | Geisler et al. | 260/239.3 A |
| 3,600,381 | 8/1971 | Yamamoto et al. | 260/239.3 A |
| 3,855,080 | 12/1974 | Becker et al. | 260/239.3 A |
| 4,107,160 | 8/1978 | Dicoi et al. | 260/239.3 A |

*Primary Examiner*—Robert T. Bond
*Attorney, Agent, or Firm*—Richard A. Anderson

[57] ABSTRACT

This invention is the method to recover caprolactam from a concentrated nylon 6 chip wash water containing water, cyclic oligomer, and caprolactam. The method comprises feeding the concentrated wash water to a wiped-film evaporator operated at a temperature of from about 200° C. to 300° C. and a pressure from about 10 to about 250 Torr, thereby separating the wash water into (a) an overhead stream of water and caprolactam and (b) a bottom stream of caprolactam and cyclic oligomers, then recovering the caprolactam from the overhead stream. The caprolactam in the bottom stream can also be recovered, and the cyclic oligomers depolymerized to caprolactam for recovery.

18 Claims, 1 Drawing Figure

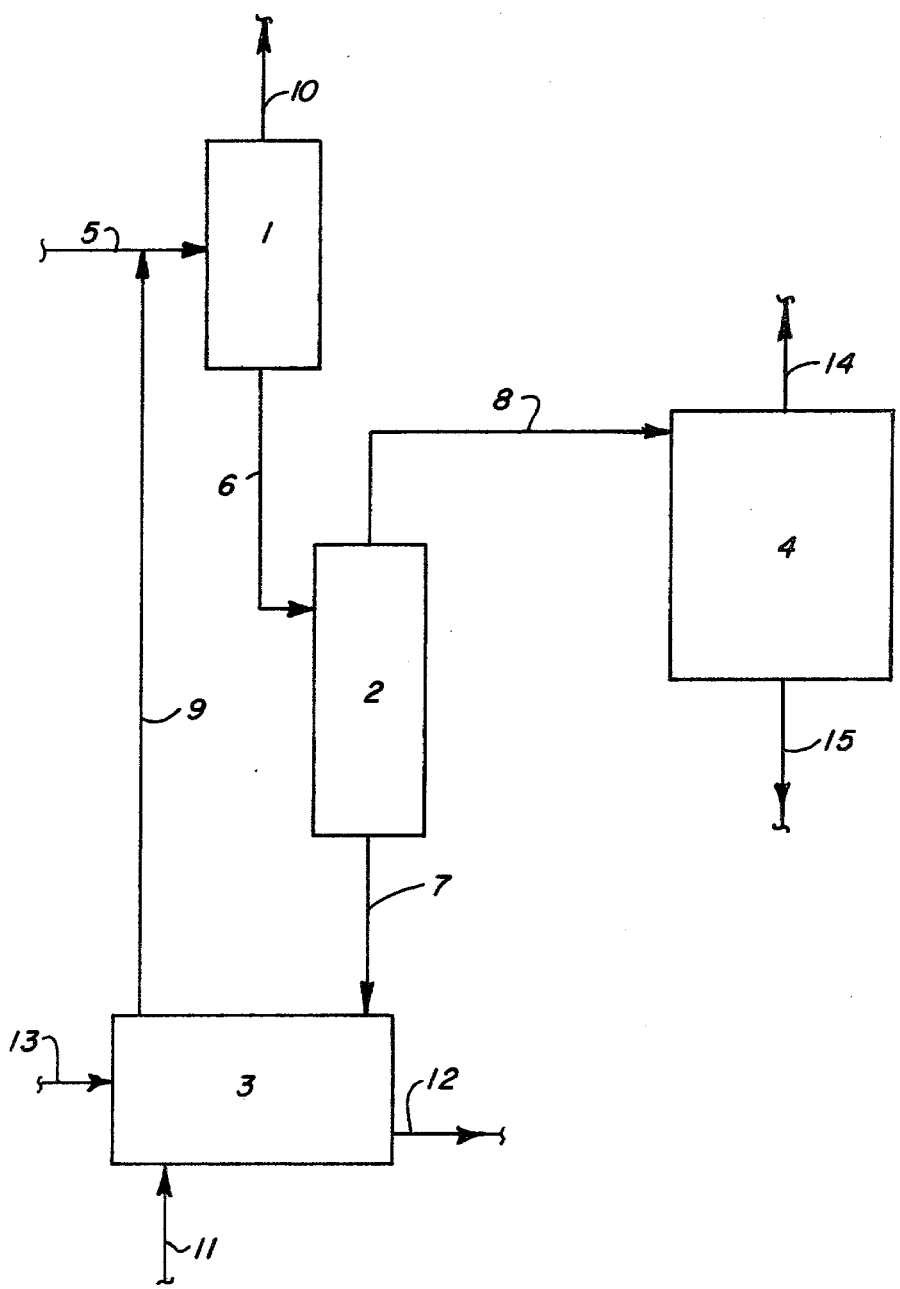

RECOVERY OF CAPROLACTAM FROM NYLON 6 OLIGOMERS

BACKGROUND OF THE INVENTION

This invention relates to the method of recovery of caprolactam from nylon 6 oligomers, more particularly from a concentrated nylon 6 chip wash water containing water, cyclic oligomer, and caprolactam.

Nylon 6 can be prepared in a continuous flow through a series of kettles, such as in U.S. Pat. No. 3,294,756, hereby incorporated by reference. The polymer resulting from this continuous kettle process is formed into pellets or chips of solid polymer containing water-extractable impurities which can be washed or extracted out of the chips by water washing, such as in U.S. Pat. Nos. 3,245,964 and 3,373,145, both hereby incorporated by reference. The washed polymer chips are then dryed, as in U.S. Pat. No. 3,266,165 hereby incorporated by reference, and are ready to be further processed such as by being fed to an extruder feeding a spinning system for spinning the polymer into fiber or yarn by conventional known methods. The resulting fiber is useful as tire and industrial yarn and as carpet or apparel yarn.

The water used to wash nylon chips contains valuable components extracted from the polymer chip such as caprolactam and cyclic lactam oligomers described in U.S. Pat. No. 3,245,964 above. Previously, only the water extracted monomer, i.e., caprolactam, was recovered from the wash water. The caprolactam was recovered by multiple distillation steps followed by multiple evaporation steps and finally crystallization of the caprolactam. The cyclic oligomer was wasted in solid residues from the bottom of the distillation and evaporation vessels.

Also, it is known to depolymerize scrap nylon, in the form of chips, yarn and the like with phosphoric acid or orthophosphoric acid in U.S. Pat. No. 3,182,055, hereby incorporated by reference.

SUMMARY OF THE INVENTION

This invention recovers, as caprolactam, the cyclic oligomer content of wash water from washing nylon 6 chips. It also effectively recovers the caprolactam from the wash water saving both capital and operating costs.

This invention is a method to recover caprolactam from a concentrated nylon 6 chip wash water containing water, cyclic oligomer, and caprolactam comprising feeding the concentrated wash water to a wiped-film evaporator operated at a temperature of from about 200° C. to 300° C. and a pressure of from about 10 to 250 Torr, thereby seperating the wash water into (a) an overhead stream of water and caprolactam and (b) a bottom stream of caprolactam and cyclic oligomers, then recovering the caprolactam from the overhead stream. The concentrated wash water contains about 5 to 50 percent by water, 5 to 12 percent by weight of cyclic oligomer, and 38 to 90 percent by weight of caprolactam. Preferably, the overhead stream from the evaporator contains above 99 percent by weight of the water fed to the evaporator and above 97 percent by weight of the caprolactam fed to the evaporator. Preferably, the bottom stream from the evaporator contains above 97 percent by weight of the cyclic oligomers fed to the evaporator and below 3 percent by weight of the caprolactam fed to the evaporator. Preferably, the concentrated wash water contains about 10 to 15 percent by weight of water, about 5 to 10 percent by weight of cyclic oligomer, and about 75 to 85 percent by weight of caprolactam.

In more detail, this invention is a method to recover caprolactam from concentrated nylon 6 chip wash water containing water, cyclic oligomer, and caprolactam comprising feeding the concentrated wash water to a wiped film evaporator operated at a temperature of from about 200° C. to 300° C. and a pressure of from about 10 to 250 Torr thereby separating the wash water into (a) an overhead stream of water and caprolactam and (b) a bottom stream of caprolactam and cyclic oligomer then recovering the caprolactam from the overhead stream and feeding the bottom stream to a depolymerization kettle at a temperature of about 230° C. to 290° C. where caprolactam is stripped off with superheated steam and recovered and the cyclic oligomer is depolymerized to caprolactam which is also removed with superheated steam and recovered. A catalyst is added to the depolymerization kettle, preferably phosphoric acid or orthophosphoric acid. The catalyst is added at a rate of about 0.5 to 5 percent by weight of the cyclic oligomer fed to the depolymerization kettle. Concentration of the catalyst in the kettle is maintained between 4 and 16 percent by weight. The caprolactam in the overhead stream from the evaporator can be recovered by evaporating the water and crystallizing the caprolactam. The caprolactam stripped off with the superheated steam from the depolymerization kettle can be recovered by being fed to a distillation column which concentrates the caprolactam. Preferably, the distillation column is the same distillation column used to produce part or all of the concentrated wash water fed to the wiped-film evaporator. The caprolactam from the evaporator and from the depolymerization kettle can be recovered by distillation to a very concentrated solution containing less than 6 percent by weight of water. Preferably, the caprolactam recovered from the depolymerization kettle is fed to the distillation column which is also used to produce the concentrated wash water and subsequently fed to the evaporator prior to being distilled to the very concentrated solution described above. The yield of cyclic oligomer depolymerized to caprolactam is above 75 percent.

Another method to recover caprolactam from the concentrated nylon 6 wash water containing water, cyclic oligomer, and caprolactam comprises feeding the concentrated wash water to a wiped-film evaporator operated at a temperature of about 200° C. to 300° C. and a pressure of from about 10 to 250 Torr thereby separating the wash water into (a) an overhead stream of water and caprolactam and (b) a bottom stream of caprolactam and cyclic oligomer and then feeding the bottom stream to a depolymerization kettle at a temperature of about 230° C. to 290° C. where caprolactam is stripped off with superheated steam and recovered and the cyclic oligomer is depolymerized to caprolactam which is also removed with superheated steam and recovered.

BRIEF DESCRIPTION OF THE DRAWINGS

The FIGURE is a schematic showing a preferred embodiment of the invention.

DESCRIPTION OF A PREFERRED EMBODIMENT

The drawing shows the preferred embodiment having four main vessels; the distillation column 1, wiped-film evaporator 2, depolymerization kettle 3, and crystallizer 4. In operation, chip wash water from various polymerization washing operations is gathered and fed through line 5 to distillation column 1 where water is distilled off to overhead line 10 and the concentrated wash water is removed through bottoms line 6 and fed to wiped-wall evaporator 2. Nearly all the remaining water and most of the caprolactam is evaporated and taken overhead through line 8 to crystallizer 4. The remaining caprolactam and nearly all of the cyclic oligomers are removed through bottoms line 7 and fed to depolymerization kettle 3. The caprolactam fed to depolymerization kettle 3 is stripped from the kettle 3 with superheated steam entering through line 11. Line 13 is to add catalyst for depolymerization such as phosphoric acid, $H_3PO_4$. The catalyst depolymerizes the cyclic oligomer charged to kettle 3 and converts it to caprolactam monomer which is stripped simultaneously with caprolactam feed from kettle 3 with superheated steam through line 11. Caprolactam from both above described sources is removed through overhead line 9 which ties into line 5 into distillation column 1 where it is concentrated as described above. Scrap nylon can also be added to kettle 3 through line 13. Caprolactam fed to crystallizer 4 is recovered as crystals in line 15 after water is evaporated off and removed through line 14. Solid residues are removed from kettle 3 through bottoms line 12. Alternatively, vessel 4 can be a distillation column which concentrates the caprolactam to a very concentrated solution of purified monomer.

EXAMPLE

Concentrated wash water from column 1 containing about 12 percent by weight water, 8 percent by weight cyclic oligomer, and 80 percent by weight caprolactam is fed at a rate of about 20 gallons per minute through line 6 to wiped-film evaporator 2. Essentially all the water in the feed and about 98.3 percent by weight of the caprolactam is removed overhead through line 8. The feed of concentrated wash water from line 6 is concentrated to a bottoms product containing about 15 percent by weight caprolactam and 85 percent by weight cyclic oligomer which is removed through line 7. Nearly all the cyclic oligomer and about 1.7 percent by weight of caprolactam fed to evaporator 2 is removed through line 7. The evaporator 2 operates at a temperature of about 280° C. and a vacuum of 100 Torr. The overhead stream through line 8 is further concentrated to crystals by evaporation in crystallizer 4. Optionally, the caprolactam could be recovered as a very concentrated solution by distillation. The bottoms stream through line 7 can be stored for treatment or disposal. Preferably, the bottoms stream through line 7 is fed as a liquid at a temperature of about 260° C. to depolymerization kettle 3. The caprolactam fed to depolymerization kettle 3 is stripped off with superheated steam through line 11. The cyclic oligomer fed to kettle 3 through line 13. About 85 percent of the cyclic oligomer is depolymerized to caprolactam. This caprolactam is also removed as it forms by the continuous stripping with superheated steam. Caprolactam from both sources goes overhead through line 9 to be concentrated through line 5 in distillation column 1. Thus, about 85 percent of cyclic oligomer is recovered as caprolactam. Formerly, this cyclic oligomer was wasted as residue in distillation column and evaporator bottoms.

The wiped-film evaporator of this invention is available commercially from Luwa and other United States or European vendors. It is a cylindrical vacuum column having rotatable blades which wipe the inside surface of the cylinder as the fed material flows through, causing formation of a thin film of material and high surface to volume ratio of material in the vessel.

ADVANTAGES

The advantages of this invention lie (1) in the capital and operating cost savings of the wiped-film evaporator and (2) in the coupling together of the wiped-film evaporator and depolymerization kettle, using the wiped-film evaporator both to recover caprolactam and provide feed for the depolymerization kettle (or reactor) and to purify the regenerated caprolactam.

1. Even when the cyclic oligomer is not depolymerized, the wiped-film evaporator replaces multiple distillation and evaporation process steps and vessels and thus lowers equipment capital and operating costs.

2. It is not necessary to attempt to recover all caprolactam in the wiped-film evaporator since this step is preferably followed by a subsequent processing step in which the remaining caprolactam is recovered via superheated steam. The bottoms leaving the wiped-film evaporator contain approximately 15 percent caprolactam. This carrier caprolactam increases the fluidity of the oligomer and makes the stream easier to handle.

3. Due to the fact that caprolactam can be left in the bottoms to fluidize the stream, it is not necessary to keep this bottom stream as hot as would be necessary without the caprolactam. This fact allows the evaporator to be operated under vacuum (100 Torr), thus lowering the temperature of the material in the evaporator. The lower material temperature creates a higher temperature differential between the jacket heating medium and the material. This larger temperature driving force allows for a reduction in the necessary heat transfer area for a required heat flow, thus allowing capital savings due to reduced equipment size.

4. The stream fed to the depolymerization kettle or reactor is at a temperature of 260° C. which is equivalent to the operating temperature of the reactor. The wiped-film evaporator serves then not only to recover caprolactam from the oligomer but also to preheat the oligomer feed to the depolymerizer, bring it up to the operating temperature of that reaction, thus conserving heat.

5. Recovery of cyclic oligomers as caprolactam lowers the amount of solid residue significantly. Disposal of the solid residue can be an economic and environmental problem.

We claim:

1. A method to recover caprolactam from a concentrated nylon 6 chip wash water containing water, cyclic oligomer, and caprolactam comprising feeding said concentrated wash water to a wiped-film evaporator operated at a temperature of from about 200° C. to 300° C. and a pressure from about 10 to about 250 Torr, thereby separating said wash water into (a) an overhead stream of water and caprolactam and (b) a bottom stream of caprolactam and cyclic oligomers, then recovering the caprolactam from the overhead stream, said bottoms stream containing only carrier lactam to increase fluidity of the oligomers and make the stream easier to handle.

2. The method of claim 1 wherein the concentrated wash water contains about 5 to 50 percent by weight water, 5 to 12 percent by weight of cyclic oligomer and 38 to 90 percent by weight of caprolactam.

3. The method of claim 1 wherein the overhead stream from the evaporator contains above 99 percent by weight of the water fed to the evaporator and above 97 percent by weight of the caprolactam fed to the evaporator.

4. The method of claim 1 wherein the bottoms stream from the evaporator contains above 97 percent by weight of the cyclic oligomers fed to the evaporator and below 3 percent by weight of the caprolactam fed to the evaporator.

5. The method of claim 1 wherein the concentrated wash water contains about 10 to 15 percent by weight of water, about 5 to 10 percent by weight of cyclic oligomer and about 75 to 85 percent by weight of caprolactam.

6. The method of claim 5 wherein the overhead stream from the evaporator contains above 99 percent by weight of the water fed to the evaporator and above 97 percent by weight of the caprolactam fed to the evaporator.

7. The method of claim 5 wherein the bottoms stream from the evaporator contains above 97 percent by weight of the cyclic oligomers fed to the evaporator and below 3 percent by weight of the caprolactam fed to the evaporator.

8. The method of claim 6 wherein the bottoms stream from the evaporator contains above 97 percent by weight of the cyclic oligomers fed to the evaporator and below 3 percent by weight of the caprolactam fed to the evaporator.

9. A method to recover caprolactam from a concentrated nylon 6 chip wash water containing water, cyclic oligomer, and caprolactam comprising feeding said concentrated wash water to a wiped-film evaporator operated at a temperature of from about 200° C. to 300° C. and a pressure from about 10 to 250 Torr, thereby separating said wash water into (a) an overhead stream of water and caprolactam and (b) a bottom stream of caprolactam and cyclic oligomers, then recovering the caprolactam from the overhead stream, and feeding the bottom stream to a depolymerization kettle at a temperature of about 230° C. to 290° C. where caprolactam is stripped off with superheated steam and recovered, and the cyclic oligomer is depolymerized to caprolactam which is also removed with superheated steam and recovered, said bottoms stream containing only carrier lactam to increase fluidity of the oligomers and make the stream easier to handle.

10. The method of claim 9 wherein a catalyst is added to the depolymerization kettle.

11. The method of claim 10 wherein the catalyst is phosphoric acid, $H_3PO_4$.

12. The method of claim 11 wherein the catalyst is added at a rate of about 0.5 to 5 percent by weight of the cyclic oligomer fed to the depolymerization kettle.

13. The method of claim 9 wherein the caprolactam in the overhead stream from the evaporator is recovered by evaporating the water and crystallizing the caprolactam.

14. The method of claim 13 wherein the caprolactam stripped off with superheated steam from the depolymerization kettle is recovered by being fed to a distillation column which concentrates the caprolactam.

15. The method of claim 14 wherein the distillation column is the same distillation column used to produce the concentrated wash water fed to the wiped-film evaporator.

16. The method of claim 9 wherein the caprolactam from the evaporator and from the depolymerization kettle is recovered by distillation to a very concentrated solution containing less than 6 percent by weight of water.

17. The method of claim 16 wherein the caprolactam recovered from the depolymerization kettle is fed to the distillation column used to produce the concentrated wash water subsequently fed to the evaporator prior to being distilled to the very concentrated solution.

18. The method of claim 9 wherein the yield of cyclic oligomer depolymerized to caprolactam is above 75 percent.

* * * * *